United States Patent
Wilcken

(10) Patent No.: US 7,869,046 B2
(45) Date of Patent: Jan. 11, 2011

(54) FULL HEMISPHERE BI-DIRECTIONAL REFLECTANCE DISTRIBUTION FUNCTION INSTRUMENT

(75) Inventor: Stephen Wilcken, Seattle, WA (US)

(73) Assignee: The Boeing Company, Chicago, IL (US)

( * ) Notice: Subject to any disclaimer, the term of this patent is extended or adjusted under 35 U.S.C. 154(b) by 542 days.

(21) Appl. No.: 11/944,352

(22) Filed: Nov. 21, 2007

(65) Prior Publication Data

US 2009/0128811 A1 May 21, 2009

(51) Int. Cl.
G01N 21/47 (2006.01)
G01B 11/24 (2006.01)
G01J 5/02 (2006.01)

(52) U.S. Cl. .............. 356/445; 356/446; 356/601; 250/340; 432/104

(58) Field of Classification Search ......... 356/445–448; 250/340; 342/104, 54, 42
See application file for complete search history.

(56) References Cited

U.S. PATENT DOCUMENTS

| | | | | |
|---|---|---|---|---|
| 5,637,873 A | * | 6/1997 | Davis et al. ............. | 250/339.11 |
| 5,784,023 A | * | 7/1998 | Bluege .................... | 342/104 |
| 6,921,898 B1 | * | 7/2005 | Chen ....................... | 250/340 |
| 7,177,026 B2 | * | 2/2007 | Perlin ...................... | 356/446 |
| 7,190,461 B2 | * | 3/2007 | Han et al. ................ | 356/446 |
| 7,689,035 B2 | * | 3/2010 | Mallick et al. .......... | 382/163 |

OTHER PUBLICATIONS

Westlund et al., "The Role of Rendering in the Competence Project in Measurement Science for Optical Reflection and Scattering", Journal of Research of the National Institute of Standards and Tehnology, vol. 107, No. 3, May-Jun. 2002.

* cited by examiner

Primary Examiner—Sang Nguyen
(74) Attorney, Agent, or Firm—Hayes Soloway P.C.

(57) ABSTRACT

According to an embodiment there is provided a bi-directional reflectance distribution function (BRDF) instrument, including an enclosure having a plurality of sides. A first side has a relatively high reflectivity substantially non-specular interior surface, while each of the remaining sides has a relatively low reflectivity interior surface. A bottom of the enclosure has a relatively low reflectivity interior surface. A viewport is formed in one of the plurality of sides or the bottom, at least one exit port is formed in at least one of the sides, and at least one entrance port is formed in at least of the sides.

10 Claims, 3 Drawing Sheets

FULL HEMISPHERE BI-DIRECTIONAL REFLECTANCE DISTRIBUTION FUNCTION INSTRUMENT

FIELD

The present disclosure is generally related to a bi-directional reflectance distribution function instrument, and more particularly is related to a bi-directional reflectance distribution function instrument capable of producing three-dimensional measurements.

BACKGROUND

Bi-directional reflectance distribution function ("BRDF") gives the reflectance of a target as a function of illumination geometry and viewing geometry. The BRDF depends on wavelength and is determined by the structural and optical properties of the surface. Optical and structural properties may include shadow-casting, multiple scattering, mutual shadowing, transmission, reflection, absorption and emission by surface elements, facet orientation distribution and facet density.

BRDF can be determined, for instance, for clouds, land cover, and radiometric boundaries, although the present disclosure is directed at determining the BRDF of samples or subjects that can be fit within an enclosure. Examples of these samples or subjects may include, for example, films or materials extracted from objects for study. The samples may generally have a small footprint. A number of devices exist for determining the BRDF of samples of this size.

One type of known device for determining the BRDF is a device that is known in the industry as a 2D BRDF. As the name implies, the BRDF is measured in two dimensions. However, to completely appreciate the BRDF results, a 3D image must be provided. A composite 3D image can be created, but it requires integrating many 2D images and recording the many 2D images is time intensive.

There also are 3D BRDF devices available in the marketplace. One such 3D BRDF device includes directing a collimated light beam against a sample within a white hemispherical screen and capturing an image of the scattered light pattern produced on the hemispherical screen by the sample. A problem with this system is that the white screen tends to re-scatter light onto other parts of the screen, which diminishes the reliability and accuracy of the 3D BRDF result. This secondary scattering of light from one part of the screen to other parts of the screen is known as cross talk.

Other known 3D BRDF devices do not include an imaging screen. These other known 3D BRDF devices are significantly more expensive while producing results that are not materially more reliable than the aforementioned 3D BRDF with a white hemispherical screen.

Thus, a heretofore unaddressed need exists in the industry to address the aforementioned deficiencies and inadequacies.

SUMMARY

Embodiments of the present disclosure provide a system, an apparatus and a method for visualizing and recording a bi-directional reflectance distribution function scattered light pattern. Briefly described, the system contains an enclosure having a plurality of sides. A first side of the plurality of sides has a relatively high reflectivity substantially non-specular interior surface, with light scattering characteristics similar to a movie screen. The remaining sides of the plurality of sides each has a relatively low reflectivity interior surface. A bottom of the enclosure has a relatively low reflectivity interior surface. A viewport is formed in one of the group consisting of the plurality of sides and the bottom. At least one entrance port for admitting a light beam is formed in at least one of the plurality of sides. At least one optional exit port may be provided in one of the group consisting of the plurality of sides to allow a light beam specularly reflected from the sample to leave the enclosure.

The present disclosure also can be viewed as providing a bi-directional reflectance distribution function instrument. The instrument comprises an enclosure having a plurality of sides. A first side of the plurality of sides has a relatively high reflectivity substantially non-specular interior surface, and a plurality of remaining sides of the plurality of sides each has a relatively low reflectivity interior surface. The bottom of the enclosure has a relatively low reflectivity interior surface. A viewport is formed in one of the group consisting of the plurality of sides and the bottom, an exit port is formed in at least one of the plurality of sides, and at least one entrance port formed in at least one of the plurality of sides.

Preferably the sides have planar or convex curvature (as viewed from the interior of the enclosure). Planar or convex curvature of the sides of the enclosure, in combination with light-absorbing coatings, limits cross-talk.

The present disclosure can also be viewed as providing methods for visualizing and recording a bi-directional reflectance distribution function scattered light pattern. In this regard, one embodiment of such a method, among others, can be broadly summarized by the following steps: directing an electromagnetic radiation beam through an entrance port on a source side of a plurality of sides of an enclosure and onto a sample; scattering the electromagnetic radiation from the sample onto at least one of the plurality of sides of the enclosure, wherein a first side of the plurality of sides has a relatively high reflectivity substantially non-specular surface and a plurality of remaining sides of the plurality of sides of the enclosure have a relatively low reflectivity surface; recording an image of the pattern of electromagnetic radiation scattered by the sample onto the first side of the plurality of sides; and scattering of the electromagnetic radiation from the first side of the plurality of sides toward at least one of the remaining sides of the plurality of sides of the enclosure.

The present disclosure also can be viewed as a system for visualizing and recording a bi-directional reflectance distribution function scattered light pattern, comprising an electromagnetic radiation source for directing an electromagnetic radiation beam into an enclosure; a sample having a textured surface for scattering the electromagnetic radiation; a relatively high reflectivity substantially non-specular surface within the enclosure for displaying the pattern of electromagnetic radiation scattered by the sample, wherein the relatively high reflectivity substantially non-specular surface is planar or convex whereby to avoid the possibility of re-scattering the electromagnetic radiation onto adjacent portions of the surface; and a camera for recording at least one characteristic of the scattered electromagnetic radiation.

BRIEF DESCRIPTION OF THE DRAWINGS

The features, functions, and advantages that have been discussed can be achieved independently in various embodiments of the present disclosure or may be combined in yet other embodiments further details of which can be seen with reference to the following description and drawings, where like reference numerals depict like parts, and wherein.

DESCRIPTION

Figure 1:
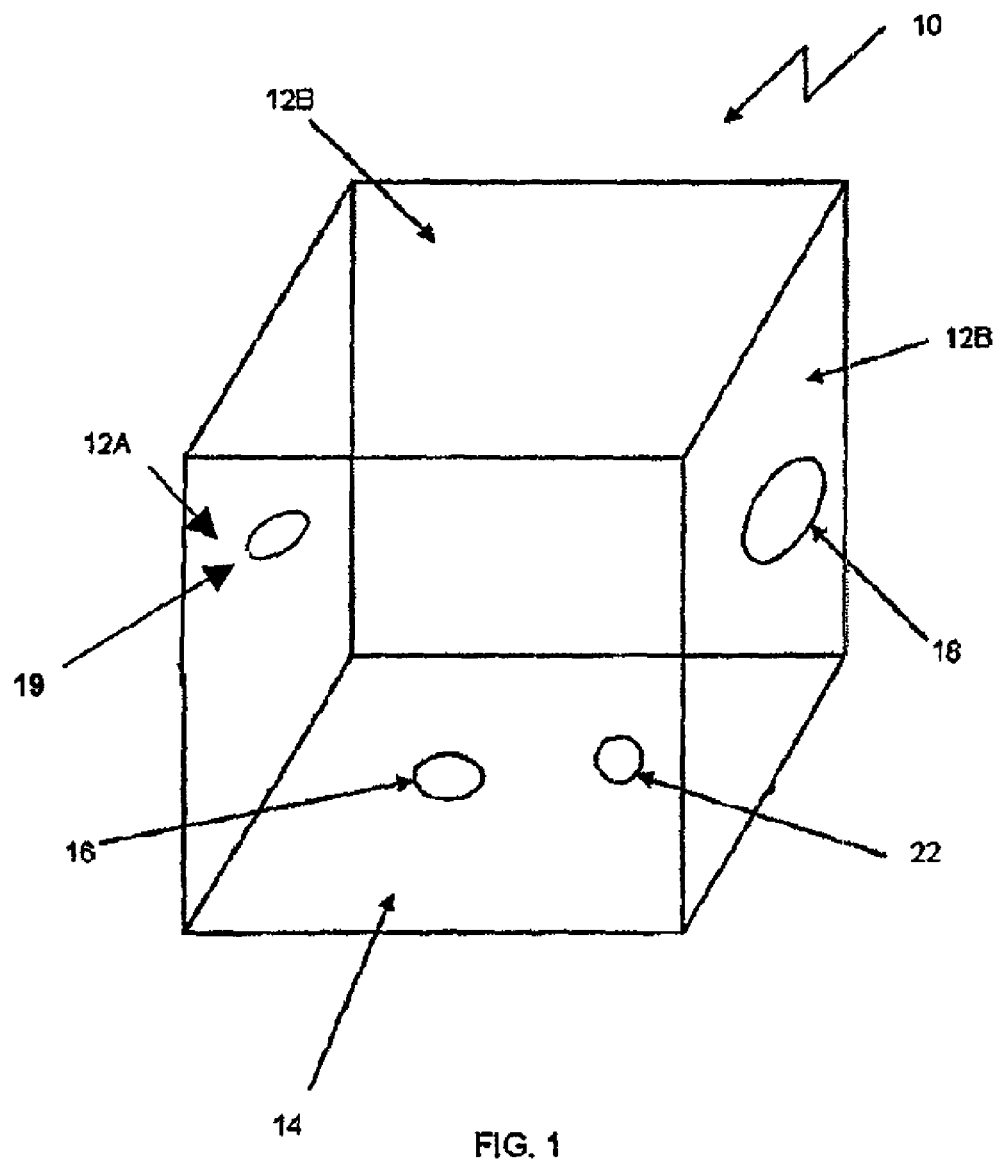
FIG. 1 is a perspective illustration of a bi-directional reflectance distribution function enclosure, in accordance with a first exemplary embodiment.

FIG. 1 is a perspective illustration of a bi-directional reflectance distribution function enclosure 10, in accordance with a first embodiment. The enclosure 10 has a plurality of sides 12A, 12B. A first side 12A has a relatively high reflectivity substantially non-specular interior surface, with light scattering characteristics similar to a movie screen. A plurality of the remaining sides 12B has a relatively low reflectivity interior surface. A bottom 14 of the enclosure 10 has a relatively low reflectivity interior surface. A camera viewport 16 is formed in one of the group consisting of the plurality of sides 12A, 12B and the bottom 14 (shown in FIG. 1 in the bottom 14). At least one entrance port 18 is formed in at least one of the plurality of sides 12. An optional exit port 19 is formed in at least one of the plurality of sides 12.

In operation, a beam of electromagnetic radiation is directed through at least one entrance view port 18 toward a sample 22. At least a portion of the beam of electromagnetic radiation is scattered toward the plurality of sides 12A, 12B of the enclosure 10. Any portion of the beam of electromagnetic radiation that is scattered toward the first side 12A will be substantially re-scattered by the non-specular but relatively high reflectivity interior surface of the first side 12A. Any portion of the beam of electromagnetic radiation that is scattered from the sample 22 toward the plurality of remaining sides 12B will be substantially absorbed/not reflected by the relatively low reflectivity interior surfaces. Any remaining non-scattered, specularly-reflected portion of the beam of electromagnetic radiation may exit the enclosure through optional exit port 19. The exit port is provided to enable further reduction of secondary scattered light within the enclosure, as might occur when a highly specular highly reflective sample is being measured. Any portion of the beam of electromagnetic radiation that is scattered from the first side 12A toward the plurality of remaining sides 12B will be substantially absorbed/not reflected by the relatively low reflectivity interior surfaces. By limiting the amount of secondarily scattered electromagnetic radiation that occurs within the enclosure 10, a clear result of bi-directional reflectance distribution is obtained. The distribution of electromagnetic radiation is recorded.

As shown in FIG. 1, a camera viewport 16 can be formed in the bottom 14. A camera may be mounted within or proximate to the camera viewport 16 to record the bi-directional reflectance distribution within the enclosure 10. The camera may have a wide-angle lens (e.g., "fish eye" lens) or something similar that permits capturing a wide field-of-view image within the enclosure 10 without a front of the camera protruding materially into the enclosure 10.

Figure 2:
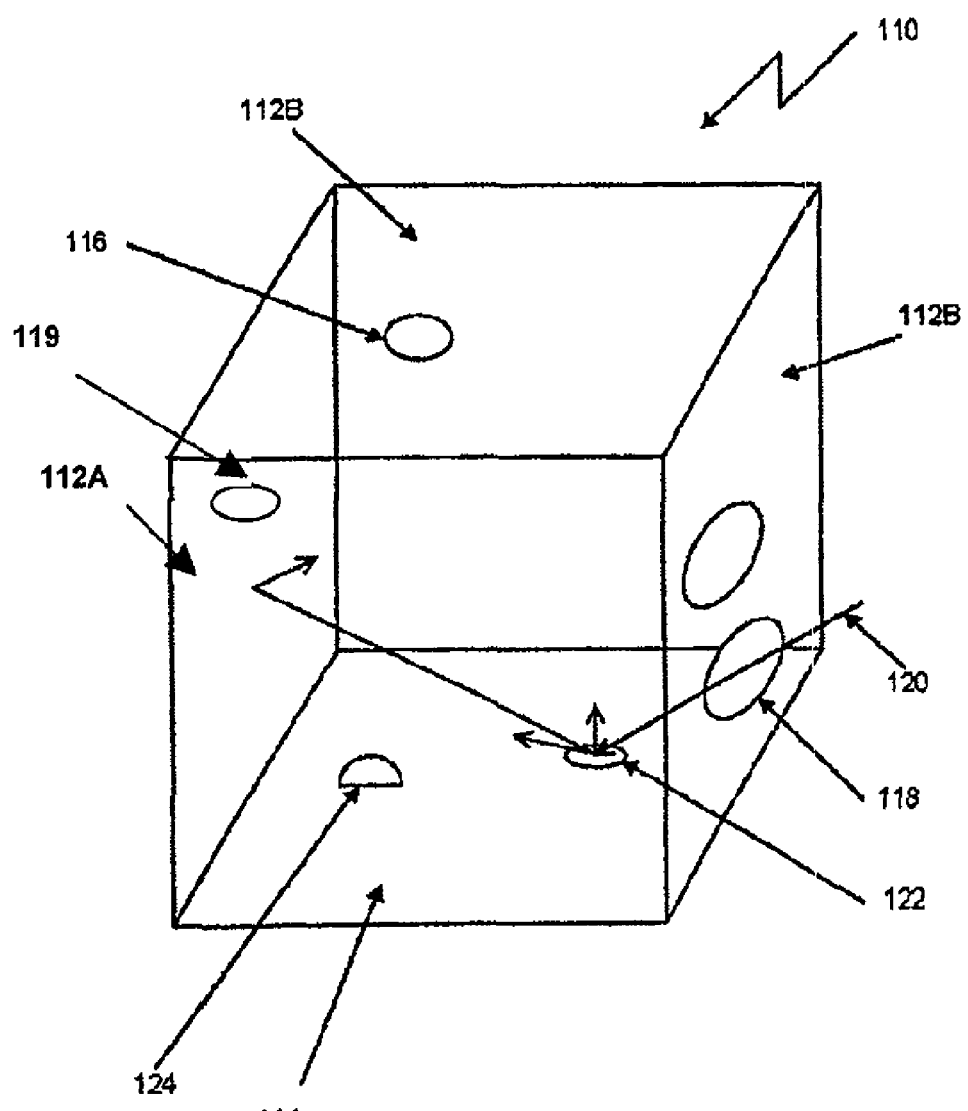
FIG. 2 is a perspective illustration of a bi-directional reflectance distribution function enclosure, in accordance with a second exemplary embodiment.

FIG. 2 is a perspective illustration of a bi-directional reflectance distribution function enclosure 110, in accordance with a second embodiment of the present disclosure. The enclosure 110 has a plurality of sides 112A, 112B. A first side 112A has a substantially non-specular but relatively high reflectivity interior surface, with light scattering characteristics similar to a movie screen. A plurality of remaining sides 112B has a relatively low reflectivity interior surface. A bottom 114 of the enclosure 110 has a relatively low reflectivity interior surface. A camera viewport 116 is formed in one of the group consisting of the plurality of sides 112A, 112B and the bottom 114 (FIG. 2 shows the camera viewport 116 in a side 112B opposite the bottom 114). At least one entrance port 118 is formed in at least one of the plurality of sides, e.g. one of sides 112B. At least one optional exit port 119 may be formed in at least one of the plurality of sides, e.g. one of sides 112A, to allow escape of electromagnetic radiation specularly reflected by the sample.

In operation, a beam 120 of electromagnetic radiation is directed through at least one entrance port 118 toward a sample 122. At least a portion of the beam 120 of electromagnetic radiation is scattered toward the plurality of sides 112 of the enclosure 110. Any portion of the beam 120 of electromagnetic radiation that is scattered toward the first side 112A will be substantially re-scattered by the relatively high reflectivity substantially non-specular interior surface of the first side 112A. Any portion of the beam 120 of electromagnetic radiation that is scattered from the sample 122 toward the plurality of remaining sides 112B will be substantially absorbed/not reflected by the relatively low reflectivity interior surfaces. Any portion of the beam 120 of electromagnetic radiation that is re-scattered from the first side 112A toward the plurality of remaining sides 112B will be substantially absorbed/not reflected by the relatively low reflectivity interior surfaces. By limiting the amount of secondary scattering of electromagnetic radiation that occurs within the enclosure 110, a clear result of the bi-directional reflectance distribution of scattered light displayed on the first side 112A is obtained. An image of the distribution of scattered electromagnetic radiation on the first side 112A is recorded.

In the embodiment shown in FIG. 2, the bi-directional reflectance distribution function enclosure 110 is substantially cube shaped. In this embodiment, each of the sides 112A, 112B is substantially planar. As the first side 112A, which has a relatively high reflectivity substantially non-specular interior surface, is planar in this embodiment, electromagnetic radiation re-scattered from the first side 112A cannot be received by another portion of the first side 112A. This physical configuration avoids the possibility of reflecting electromagnetic radiation onto itself (i.e., crosstalk), as would occur if the first side 112A were concave as viewed from the interior of the enclosure. The hemispherical enclosure known in the prior art is a limiting case comprising undesirable concave curvature. Elimination of cross-talk may also be achieved by making the first side 112A convex. Also, while the cube shaped-design allows each of the sides to have substantially equivalent dimensions, the bi-directional reflectance distribution function enclosure 110 can be constructed in the form of a less symmetric shape and may have fewer than 6 sides or more than 6 sides.

In operation, once the distribution of electromagnetic radiation is recorded, the first side 112A is relocated. More specifically, a different side 112B of the bi-directional reflectance distribution function enclosure 110 is provided with a relatively high reflectivity substantially non-specular interior surface and the side that had the relatively high reflectivity substantially non-specular interior surface during the recording of the scattered electromagnetic radiation distribution is provided with a relatively low reflectivity interior surface. This reorientation of the sides of the bi-directional reflectance distribution function enclosure 110 can be accomplished in a number of different ways, all of which are considered to be within the scope of the present disclosure. One way to reorient the sides of the bi-directional reflectance distribution function enclosure 110 would be to make each of the sides removable and reversible, with each side having a relatively high reflectivity substantially non-specular surface on one face and a relatively low reflectivity interior surface on an opposite face. In this regard, to reorient the bi-directional reflectance distribution function enclosure 110, the first side 112A could be reversed to allow a relatively low reflectivity surface of the first side 112A to face the interior of the bi-directional reflectance distribution function enclosure 110 and one of the remaining sides 112B could be reversed to have its relatively high reflectivity substantially non-specular surface face the interior of the bi-directional reflectance distribution function enclosure 110.

As shown in FIG. 1, a camera viewport 16 can be formed in the bottom 14. Another possibility, shown in FIG. 2, is to place a substantially hemispherical mirror 124 integral with the bottom 114 and place the camera viewport 116 in a top side 112B of the plurality of sides, approximately above the hemispherical mirror 124. The camera may visually record the bi-directional reflectance distribution along the sides 112A, 112B based on an image reflected by the hemispherical mirror 124. Those having ordinary skill in the art may conceive of other permutations for positioning one or more cameras and one or more mirrors to record the bi-directional reflectance distribution along the sides 112A, 112B and all such permutations are considered to be within the scope of the present disclosure.

It should be noted that the bottom 114 is an arbitrary title. It is possible that the bottom 114 of the enclosure 110 is on the side or top of the enclosure 110. The purpose of the bottom 114 is to receive the sample 122. It may be preferable, particularly as sides 112A, 112B are changed out or reoriented, to leave the bottom 114 as the lowest side of the enclosure 110, but the scope of the disclosure is not limited to this configuration.

The beam 120 may emanate from at least one electromagnetic radiation source positioned to direct the beam 120 at the sample 122 through at least one of the entrance ports 118. The embodiment of the disclosure shown in FIG. 2 may allow beam 120 to project at an angle of as little as or less than 5 angular degrees relative to the bottom 114 and still provide meaningful bi-directional reflectance distribution data. Multiple entrance ports 118 may be provided and data may be collected by projecting the beam 120 through each of the entrance ports 118 toward the sample 122 for separate data recordings. The beam 120 of electromagnetic radiation may be a collimated light beam. Multiple exit ports 119 provide the means for the portion of the incident collimated light beam specularly reflected by the sample to leave the interior of the enclosure 110, thus further limiting the intensity of secondarily scattered light within the enclosure 110.

Figure 3:
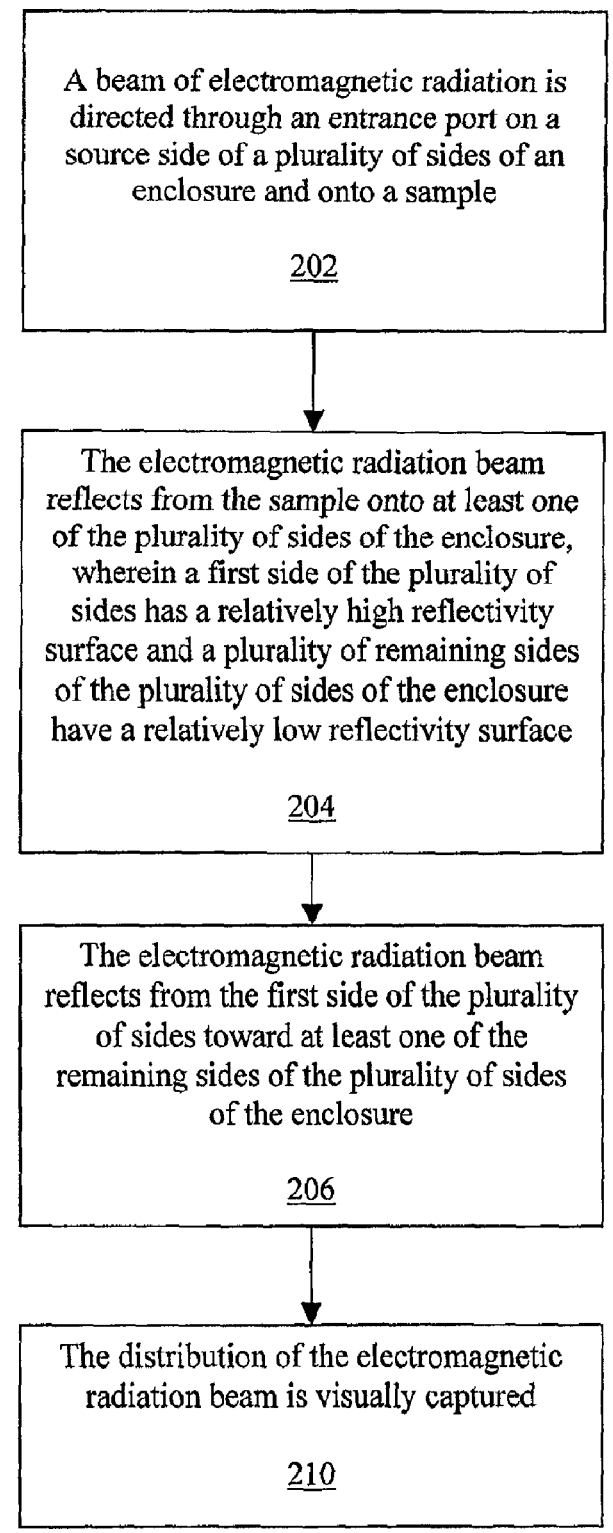
FIG. 3 is a flowchart illustrating a method of utilizing the abovementioned bi-directional reflectance distribution function enclosure in accordance with the second exemplary embodiment.

FIG. 3 is a flowchart 200 illustrating a method of utilizing the above mentioned bi-directional reflectance distribution function enclosure 110 in accordance with the second embodiment of the disclosure. It should be noted that any process descriptions or blocks in flow charts should be understood as representing modules, segments, portions of code, or steps that include one or more instructions for implementing specific logical functions in the process, and alternate implementations may be included in which functions may be executed out of order from that shown or discussed, including substantially concurrently or in reverse order, depending on the functionality involved, as would be understood by those reasonably skilled in the art.

As is shown by block 202, a beam 120 of electromagnetic radiation is directed through an entrance port 118 on a source side of a plurality of sides 112A, 112B of an enclosure 110 and onto a sample 122. The electromagnetic radiation beam 120 scatters from the sample 122 onto at least one of the plurality of sides of the enclosure 110, wherein a first side 112A of the plurality of sides has a relatively high reflectivity substantially non-specular surface and a plurality of remaining sides 112B of the plurality of sides of the enclosure 110 have a relatively low reflectivity surface (block 204). The electromagnetic radiation scattered by sample 122 is re-scattered from the first side 112A of the plurality of sides toward at least one of the remaining light-absorbing sides 112B of the plurality of sides of the enclosure 110 (block 206). The image of the distribution of the scattered electromagnetic radiation derived from beam 120 is recorded (block 208).

Utilizing the enclosure 110 may also include changing the relatively high reflectivity substantially non-specular surface of the first side 112A of the plurality of sides to a relatively low reflectivity surface and changing a relatively low reflectivity surface of a second side 112B of the plurality of sides to a relatively high reflectivity substantially non-specular surface. Once the sides 112A, 112B have been reoriented, the image of the distribution of the scattered electromagnetic radiation is recorded. Preferably, this step is repeated until each of the five non-bottom sides (in the 6-sided form of the enclosure 110) has been changed and images of the scattered light patterns on the interior-facing sides of the plurality of sides pertaining to the five permutations has been recorded. Changing the sides 112A, 112B may involve reversing the sides, wherein each side has a relatively low reflectivity surface and a relatively high reflectivity substantially non-specular surface, or substituting new sides for the sides in use. Other methods of manipulating the sides 112A, 112B such that the relatively low reflectivity surfaces and the relatively high reflectivity substantially non-specular surfaces are changed are envisioned and within the scope of those with ordinary skill in the art and all such methods of manipulating the sides 112A, 112B are considered to be within the scope of the present disclosure.

Once multiple images of the distribution of the electromagnetic radiation have been captured, the images may be stitched together utilizing conventional image processing software. Preferably, the number of images stitched together is equivalent to the number of sides, however fewer images may be stitched together to achieve an understanding of the bi-directional reflectance distribution. Furthermore, samples which have known or well understood optical scattering characteristics (e.g., samples coated with a reflectance calibration standard such as Spectrolon®, available from Labsphere, Inc., North Sutton, N.H.) may be used as reference standards. The process of recording the BRDF of the standard, and the use of such recorded BRDF data for removing or accommodating instrumental characteristics of the enclosure and data recording mechanisms through standard data renormalization or rectification procedures, will be familiar to those skilled in the art.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and protected by the following claims.

What is claimed is:

1. A method of visualizing and recording a bi-directional reflectance distribution function scattered light pattern, comprising the steps of:
   directing an electromagnetic radiation beam through an entrance port on a source side of a plurality of sides of an enclosure and onto a sample;
   scattering the electromagnetic radiation beam from the sample onto at least one of the plurality of sides of the enclosure, wherein a first side of the plurality of sides has a relatively high reflectivity substantially non-specular surface and a plurality of remaining sides of the plurality of sides of the enclosure have a relatively low reflectivity or light-absorbing surface;
   re-scattering the electromagnetic radiation from the first side of the plurality of sides toward at least one of the remaining light-absorbing sides of the plurality of sides of the enclosure; and
   recording the distribution of the scattered electromagnetic radiation by a camera.

2. The method of claim 1, further comprising the steps of:
   exchanging the relatively high reflectivity substantially non-specular surface of the first side of the plurality of sides for a relatively low reflectivity surface;
   exchanging the relatively low reflectivity surface of a second side of the plurality of sides for a relatively high reflectivity substantially non-specular surface; and
   recording the distribution of the scattered electromagnetic radiation in an image before and after exchanging the first and second sides.

3. The method of claim 2, wherein the step of exchanging the relatively high reflectivity substantially non-specular surface of the first side further comprises removing the first side of the plurality of sides and replacing the first side with a side having a relatively low reflectivity light-absorbing surface.

4. The method of claim 2, wherein the first side of the plurality of sides has a first face with a relatively high reflectivity substantially non-specular surface and a second face with the relatively low reflectivity light-absorbing surface and the step of exchanging the relatively high reflectivity substantially non-specular surface for the relatively low reflectivity light-absorbing surface comprises flipping the sides.

5. The method of claim 2, further comprising the step of stitching together visually captured images of the distribution of the scattered electromagnetic radiation, utilizing image processing software.

6. The method of claim 2, further comprising the step of utilizing a sample with well known BRDF characteristics as a means for instrumental calibration.

7. The method of claim 2, further comprising manipulating each of the sides of the plurality of sides wherein the distribution of the scattered electromagnetic radiation is recorded on multiple occasions including occasions in which each side of the plurality of sides has a relatively high reflectivity substantially non-specular surface while the other sides of the plurality of sides has a relatively low reflectivity light-absorbing surface.

8. The method of claim 2, wherein the distribution of the scattered electromagnetic radiation is recorded using a camera.

9. A system for visualizing and recording a bi-directional reflectance distribution function scattered light pattern, comprising:
   an electromagnetic radiation source for directing an electromagnetic radiation beam into an enclosure;
   a sample having a textured surface for scattering the electromagnetic radiation;
   a relatively high reflectivity substantially non-specular surface within the enclosure for displaying the pattern of electromagnetic radiation scattered by the sample, wherein the relatively high reflectivity substantially non-specular surface is planar or convex whereby to avoid the possibility of re-scattering the electromagnetic radiation onto adjacent portions of the surface; and
   a camera for recording at least one characteristic of the scattered electromagnetic radiation.

10. The system of claim 9, wherein the relatively high reflectivity substantially non-specular surface is moveable within the enclosure.

* * * * *